United States Patent [19]

Zenk et al.

[11] 4,329,361
[45] May 11, 1982

[54] USE OF ROSMARINIC ACID IN THE TREATMENT OF INFLAMMATIONS AND PHARMACEUTICAL PRODUCTS USED THEREIN

[75] Inventors: Meinhard Zenk, München-Pasing; Eugen Etschenberg, Cologne; Erich Graf, Kerpen, all of Fed. Rep. of Germany

[73] Assignee: Nattermann & Cie GmbH, Cologne, Fed. Rep. of Germany

[21] Appl. No.: 215,421

[22] Filed: Dec. 11, 1980

[30] Foreign Application Priority Data

Dec. 22, 1979 [DE] Fed. Rep. of Germany ....... 2952114

[51] Int. Cl.³ .............................................. A61K 31/19

[52] U.S. Cl. ..................................................... 424/317
[58] Field of Search ......................................... 424/317

[56] References Cited

PUBLICATIONS

Chem. Abst. 82-161491 (1975).

*Primary Examiner*—Stanley J. Friedman
*Attorney, Agent, or Firm*—Pearne, Gordon, Sessions, McCoy & Granger

[57] ABSTRACT

The present invention is directed to a new process for the treatment of inflammatory diseases and disorders in humans by administering a pharmaceutical preparation containing rosmarinic acid.

2 Claims, No Drawings

USE OF ROSMARINIC ACID IN THE TREATMENT OF INFLAMMATIONS AND PHARMACEUTICAL PRODUCTS USED THEREIN

There have been proposed already a great number of products for the treatment of inflammatory diseases and disorders. For instance, there may be used steroides, various pyrazolone derivatives or various derivatives of phenyl acetic acid, phenyl propionic acid or indol acetic acid, in particular indometacin.

However, all anti-inflammatory products used at present have the disadvantage to show one or several serious disadvantages such as heart-burn, formation of ulcera or even gastrointestinal bleeding.

It is therefor an object of the present invention to find new products which have a low toxicity and an excellent compatibility to the stomach.

It has been surprisingly found that rosemarinic acid, i.e. 3.4-dihydroxy-α-[[3-(3.4-dihydroxyphenyl)-1-oxo-2-propenyl]-oxy]-phenylpropionic adid, which occurs in natur, shows an excellent antiphlogistic activity and has a substantially increased range of therapeutic application in comparison to the known compounds in this field. Furthermore, rosmarinic acid does not produce any ulcus in the stomach and therefor can be administered also to patients showing a high gastrointestinal incompatibility without endangering the same.

Rosmarinic acid occurs in various plants such as Rosmarinus officinalis (see Ricerca sci. 1958, vol. 28, p. 2329 to 2333), Melissa officinalis (see Arch. Pharm. 1960, vol. 293, p. 1043 to 1048) or Teucrium scorodonia (see Planta Med. 1965, vol. 13, 3, p. 331 to 345) and other plants. Rosmarinic acid may be recovered from such plants by extraction. Furthermore, rosmarinic acid may also be recovered from plant cell cultures of Coleus blumei (see Naturwissenschaften 1977, vol. 64, 11, p. 585 to 586).

Extracts containing rosmarinic acid have been tested for a stimulating activity upon the circulation of the blood (see Deutsche Apotheker Zeitung 1964, vol. 104 (10), p. 257 to 259) and for antimicrobial activity (see N. Z. Alimkhodzhaeva et al., CA 82/161491). An antiphlogistic activity has never been found and described up to now.

The antiphlogistic activity of rosmarinic acid is determined in the rat paw edema test according to Hillebrecht (see J. Hillebrecht, Arzneim. Forschung 1954, vol. 4, p. 607). In this test an edema is produced in one of the hindpaws of rats weighing 200 to 250 g by subplantaneous administration of Carragenin in an amount of 0.1 cc. of solution per paw containing 0.5% Carragenin in a 0.9% NaCl solution. After administration of the tested compound which in general should not exceed a volume of 10 cc. per kg of body weight, the volume of the paw is determined in a overflowing water container. Three hours after administration the final volume of the paw is determined. For each dose there are tested 10 test animals and 10 control animals of identical sex and the test is repeated with the same number of test animals and control animals of the other sex. For evaluation, the percent of retardation of edema formation is compared over the edema formation in the control group.

Rosmarinic acid in the treatment of humans suffering from inflammatory diseases and disorders is administered in daily doses ranging from 50 to 1000 mg, preferably from 100 to 500 mg.

The following test results were obtained:

TABLE 1

|                        | Rosmarinic acid |      |      | Indometacin |      |      |
|------------------------|-----------------|------|------|-------------|------|------|
| Dose (mg/kg i.m.)      | 0.1             | 1.0  | 10.0 | 3.2         | 5.6  | 8.3  |
| % degrees of edema formation | −22       | −31  | −22  | −23         | −36  | −52  |

Ulcus formation is determined according to W. J. R. Whittle (see Brit. J. Pharmacology 1975, vol. 55, p. 242 to 243), L. Mariani (see Europ. J. Toxicol. Eviron, 1975, vol. 8, p. 335 to 339) and R. Menguy and L. Desbaillets (see Proc. Soc. Exp. Bio., vol. 125, p. 1108).

In this test there are used 10 female and 10 male wistar rats (120 to 150 g which have been kept fasting for 16 hours) per each dose. A bleeding ulcus of the stomach was provocated by oral application of the test compound. 3.5 hours after administration the rats were killed, the stomach taken out, opened along the large curvature and fixed to a Styropor plate. The mean ulcus formation was determined for the test group and for the control group.

TABLE 2

| Ulcus producing activity in rats | | | | | | |
|---|---|---|---|---|---|---|
| | Rosmarinic acid | | | Indometacin | | |
| Dose (mg/kg p.o.) | 10 | 100 | 316 | 3.2 | 5.6 | 7.5 |
| Activity | 0 | 0 | 0 | ++ | +++ | +++ |

0 = no ulcus formation
+ = slight ulcus formation
++ = considerable ulcus formation
+++ = very high ulcus formation The toxicity was determined in the mouse.

TABLE 3

|                   | Rosmarinic acid | Indometacin |
|-------------------|-----------------|-------------|
| Dose (mg/kg i.m.) | 316             | 18          |
| % mortality       | 0               | 50          |

As follows from the above results, rosmarinic acid has an excellent antiphlogistic activity at very low doses, has no ulcus forming activity at all and only a very low toxicity.

Pharmaceutical preparations containing rosmarinic acid may be readily produced by mixing the active dose of rosmarinic acid with suitable inorganic or organic, solid or liquid pharmaceutical carrier materials which may be administered enterally or parenterally.

Thus, tablets or gelatine capsules may be produced which contain the active compound together with diluents such as lactose, dextrose, sucrose, mannitol, sorbitol, cellulose and/or glycerin and lubricants such as silica, talcum, stearic acid or salts thereof, such as magnesium or calcium stearate and/or polyethylene glycol. Tablets also may contain binding agents such as magnesiumaluminumsilicate, corn starch, wheat starch or rice starch, gelatine, methylcellulose, sodium carboxymethylcellulose and/or polyvinyl pyrrolidone and, if desired, expander agents such as agar, alginic acid or salts thereof such as sodium alginate and/or effervescent mixtures or absorbents, dyestuffs, flavouring agents and sweeteners. Furthermore, rosmarinic acid may be used in injectable preparations such as intravenously administerable solutions or infusion solutions. Such solutions preferably represent isotonic aqueous solutions or suspensions which may be produced from lyophylisized products containing the active compound alone or together with carrier materials. The pharmaceutical preparations may be produced in usual manners for instance by mixing, granulating, dragee formation, dissolving or lyophilisation.

EXAMPLE 1

25 mg of rosmarinic acid are dissolved in 1 ml of a physiological sodiumchloride solution. The resulting solution is sterilized by means of membrane filtration and filled into an ampoule under sterile conditions.

EXAMPLE 2

Rosmarinic acid containing tablets:

50 mg of rosmarinic acid, 150 mg of microcristalline cellulose, 50 mg of Aerosil (a powderous silicic acid product containing 99.9% of $SiO_2$ produced by the company Degussa AG of Frankfurt/Main, Federal Republic of Germany) and 15 mg of Cutina HR are thoroughly mixed, pressed to tablets and the tablets are coated with a film of 20 mg of hydroxypropylmethylcellulosephthalate.

EXAMPLE 3

Rosmarinic acid capsules:

50 mg of rosmarinic acid, 5 mg of talcum, and 10 mg of Aerosil 200 are thoroughly mixed, granulated and filled into gelatine capsules.

What we claim is:

1. A method for the treatment of humans suffering from inflammatory diseases and disorders comprising administering to said humans a pharmaceutical preparation containing rosmarinic acid, in a daily dose ranging from 50 to 1000 mg of rosmarinic acid.

2. A method as set forth in claim 1 wherein said pharmaceutical preparation of rosmarinic acid is administered in a daily dose ranging from 100 to 500 mg of rosmarinic acid.

UNITED STATES PATENT AND TRADEMARK OFFICE
CERTIFICATE OF CORRECTION

PATENT NO. : 4,329,361

DATED : May 11, 1982

INVENTOR(S) : Meinhard Zenk et al.

It is certified that error appears in the above—identified patent and that said Letters Patent is hereby corrected as shown below:

Column 1, line 21, delete "adid" and substitute therefor --acid--; and

Column 1, line 22, delete "natur" and substitute therefor --nature--.

Signed and Sealed this

Fourteenth Day of June 1983

[SEAL]

Attest:

DONALD J. QUIGG

Attesting Officer    Acting Commissioner of Patents and Trademarks